United States Patent [19]
Budzynski et al.

[11] Patent Number: 5,288,490
[45] Date of Patent: Feb. 22, 1994

[54] THROMBUS-TARGETED COMPLEXES OF PLASMINOGEN ACTIVATOR AND FIBRIN FRAGMENTS

[75] Inventors: Andrei Z. Budzynski, Glenside, Pa.; Linda C. Knight, East Windsor, N.J.; Ahmed A. Hasan, Glenside, Pa.

[73] Assignee: Temple University of the Commonwealth System of Higher Education, Philadelphia, Pa.

[21] Appl. No.: 799,699

[22] Filed: Nov. 25, 1991

Related U.S. Application Data

[63] Continuation of Ser. No. 356,978, May 24, 1989, abandoned.

[51] Int. Cl.$^5$ .................... A61K 37/547; A61K 37/18
[52] U.S. Cl. ............................. 424/94.64; 424/94.3; 435/219; 435/226; 514/2
[58] Field of Search .................. 424/94.63, 94.64, 94.3; 435/68.1, 212, 215, 216, 219, 226; 514/2, 381; 530/381, 382, 830

[56] References Cited

U.S. PATENT DOCUMENTS

| | | | |
|---|---|---|---|
| 4,427,646 | 1/1984 | Olexa et al. | 424/1.1 |
| 4,536,391 | 8/1985 | Miyazaki et al. | 424/94.64 |
| 4,564,596 | 1/1986 | Maximenko et al. | 435/177 |
| 4,673,573 | 6/1987 | Ferres et al. | 424/94.63 |

OTHER PUBLICATIONS

Bode et al., *Science* 229:765–767 (1985).
Bode et al., *J. Biol. Chem.* 262:10819–10823 (1987).
Bode et al., *J. Mol. Cell Cardiol.* 19:335–341 (1987).
de Munk et al, Biochemistry (1989) 28 7318–7325.
Takada et al, Biol. Abstracts vol. 86(7), Oct. 1988, No. 66184.
Takada et al., "Enhanced Activator Activity of the Mixture of Streptokinase and a Modified Form of PLasminogen (Lys-Plasminogen) in the Presence of Fibrin: Role of Conformational Change of Plasminogen" Haemostasis 18, 106 112 (1988).
Olexa et al., *Proc. Natl. Acad. Sci. USA* 77: 1374–1378 (1980).
Knight et al., *J. Clin. Invest.* 72:2007–2013 (1983).
Knight et al., *Radiology* 156:506–514 (1985).
Nieuwenhuizen et al., *Biochem. Biophys. Acta* 755:531–533 (1983).
Lijnen et al., *Eur. J. Biochem.* 144:541–544 (1984).
Nieuwenhuizen et al., *Biochem. Biophys. Acta* 748:86–92 (1983).

*Primary Examiner*—Jacqueline Stone
*Attorney, Agent, or Firm*—Seidel, Gonda, Lavorgna & Monaco

[57] ABSTRACT

Thrombolytic hybrids are formed as covalent or non-covalent complexes of fibrin fragments and plasminogen activator molecules. Native plasmin degradation fragments of fibrin or non-native fibrin fragments are covalently or non-covalently linked to plasminogen activators such as t-PA, scu-PA, urokinase, streptokinase, and the like. Useful native fibrin fragments which may be utilized to form complexes with plasminogen activators include fragments $E_1$, $E_2$, $E_3$, D and DD, and (DD)E complex. The fibrin fragment component targets the hybrid to vascular thrombi, immobilizing the plasminogen activator molecule onto the fibrin surface of the thrombus. Once localized on a thrombus surface, the plasminogen activator component of the hybrid activates only the clot-surface bound plasminogen transported by the fibrin fragment vehicle, without significant systemic activation of plasminogen. The hybrids are strong potentiators of plasminogen activator activity, generating more plasmin from fibrin-surface bound plasminogen than the plasminogen activator molecule alone. The hybrids have a longer half-life in circulation than the corresponding unprotected plasminogen activator molecules.

15 Claims, 7 Drawing Sheets

THROMBUS-TARGETED COMPLEXES OF PLASMINOGEN ACTIVATOR AND FIBRIN FRAGMENTS

REFERENCE TO GOVERNMENT GRANT

The invention described herein was supported in part by National Institutes of Health Grant HL 36221.

This is a continuation of co-pending application Ser. No. 07/356,978 filed on May 24, 1989, abandoned.

FIELD OF THE INVENTION

The invention relates to novel agents for thrombolytic therapy, more particularly to hybrids formed by joining plasminogen activators and fibrin fragments.

BACKGROUND OF THE INVENTION

A safe, effective method of dissolving vascular thrombi is urgently needed, owing to the life-threatening complications of thromboembolic disease. The most common of such disorders is the formation of thrombi, in a blood vessel or heart cavity that remain at the point of formation. Thrombi in heart vessels, for example, can restrict blood flow, resulting in myocardial infarction. Coronary arteriographic studies indicate that 87% of transmural myocardial infarctions are caused by occlusive coronary artery thrombosis. DeWood et al., *N. Eng. J. Med.* 303:397–902 (1980).

In addition, parts of a thrombus may dislodge from its point of attachment and move through the blood vessels until it reaches a point where passage is restricted. The resulting blockage is known as a thromboembolism.

Plasminogen activators function mainly by converting the zymogen plasminogen into plasmin, which is regarded as the end stage non-specific proteolytic enzyme in fibrinolysis. Plasmin lyses the fibrin matrix and acts on other components of the thrombus as well. The efficiency of the lytic activity of exogenous plasminogen activator depends significantly on the amount of plasmin it generates from endogenous plasminogen, which is present in free-form in circulating blood and bound form on the fibrin surfaces of thrombi and hemostatic plugs. In any thrombolytic therapy, it is desirable to generate the maximum amount of plasmin on the fibrin surface i.e., plasmin immobilized on the thrombus, with a minimum quantity of plasmin (if possible, none at all) in the circulating blood. While immobilized plasmin efficiently carries out the lysis of the thrombus and helps establish reperfusion, circulating plasmin exhibits fibrinogenolytic activity, degrades platelet receptors, digests thrombospondin, and consequently decreases the platelet aggregation capacity of the patient. The result is the so called "lytic state", which is accompanied by various undesired complications.

A variety of plasminogen activators have been utilized to promote dissolution of thrombi and restoration of blood circulation to blocked vessels. However, the available plasminogen activators are far from ideal. Streptokinase, which is of bacterial origin, is antigenic. A loading dose is needed to neutralize pre-existing anti-streptokinase antibodies. Streptokinase treatment must be limited in duration because of an increase in such antibody levels. Conard et al., *Semin. Throm. Haemostas.* 13:212–222 (1987). Streptokinase works efficiently to dissolve thrombi if administered locally, but local administration requires catheterization, which may often preclude administration promptly enough to provide significant benefit to the patient. Systemic administration of streptokinase in acute myocardial infarction causes an undesirable side effect by degrading fibrinogen and severely depleting plasminogen in the circulation. Mentzer et al., *Am. J. Cardiol.* 57:1220–1226 (1986).

Another widely used plasminogen activator, urokinase, is available in three forms. So called "two-chain urokinase" (hereinafter "urokinase") can be extracted from human urine or prepared from kidney cell cultures. Another form, "single-chain urokinase" or "pro-urokinase" (hereinafter "scu-PA"), a precursor of urokinase, has been isolated from human fluids and also obtained by recombinant DNA technology. A low molecular weight form of urokinase is obtained from long plasmin digestion of two-chain urokinase.

Although urokinase is not antigenic, its mechanism of plasminogen activation parallels that of streptokinase, resulting in a significant fibrinogenolytic response in the circulating blood. Single-chain urokinase has promising characteristics. However, it has not yet been adequately tested in man. In a small study of normal human subjects, scu-PA displayed fibrinolytic activity comparable to urokinase, and a lower systemic action than urokinase. Trubestein et al., *Hemostasis* 17:238–244 (1987).

Non-urokinase plasminogen activators, which include tissue plasminogen activator ("t-PA"), are physiologic activators of plasminogen which may be manufactured by cell culture and genetic engineering. t-PA is capable of binding fibrin, and is believed to convert plasminogen to plasmin at the fibrin surface. Thus, it works more efficiently than streptokinase or urokinase when administered systemically. However, initial clinical trials indicate that lysis of fibrinogen is still significant during administration of t-PA. Sherry, *N. Engl. J. Med.* 313:1014–1017 (1985).

Although it has high specificity for fibrin, t-PA has certain limitations. It has a very short biological half-life time in the circulation of humans, on the order of five minutes. Cellular clearance of t-PA by the liver is believed responsible for this limited biological half-life time. Rapid decrease of t-PA in the blood after intravenous administration constitutes a major difficulty in drug therapy with respect to maintaining an adequate concentration of the activator.

Plasma contains plasminogen activator inhibitors which can bind and inactivate plasminogen activators. Continuous infusion of large doses of t-PA are therefore necessary to overcome the effect of these inhibitors. At physiologic levels, free t-PA is bound by the plasma inhibitor, PAI-1. Wun et al., *Blood* 69:1354–1362 (1987). The latter has shown to be present in elevated levels in the plasma of patients with myocardial infarction, Hamsten et al., *N. Engl. J. Med.* 313:1557–1563 (1985); recurrent deep venous thrombosis, deJong et al., *Thromb. Haemostas.* 57:140–143 (1987); and coronary artery disease, Paramo et al., *Br. J. Med.* 291:573–574 (1985). When purified t-PA is added to plasma to create higher-than physiologic levels to overcome the inhibitory effect of PAI-1, it complexes with other inhibitors present in plasma, such as C1-inhibitor, alpha$_2$-antiplasmin and macroglobulin. Thorsen et al., *Biochem. Biophys. Acta* 802:111–118 (1984); Rijken et al., *J. Lab. Clin. Med.* 101:285–294 (1983); Kruithoff et al., *Blood* 64:907–913 (1984).

Administration of urokinase, streptokinase and t-PA results in an increased tendency for bleeding, limiting the usefulness of these agents, particularly during surgical procedures.

Streptokinase and urokinase do not have inherent fibrin specificity. They indiscriminately convert both circulating and fibrin-surface bound plasminogen into plasmin at presently-used therapeutic dosages. While t-PA and scu-PA have fibrin specificity, they have short half-life times in the blood. A high dosage must be infused over a long period of time in order to maintain a therapeutic concentration in the blood. Consequently, hemostatic imbalances are encountered. Moreover, since the specificities of t-PA and scu-PA for fibrin are not absolute, they leave a small amount of activators in the liquid phase, and some amount of plasmin is gradually produced in the circulating blood.

Complexes have been formed from urokinase and antifibrin murine monoclonal antibodies. Bode et al., *Science* 229:765-767 (1985); Bode et al., *J. Biol. Chem.* 262:10819-10823 (1987) and *J. Mol. Cell Cardiol.* 19:335-341 (1987). In an in vitro model of a thrombus in a circulating plasma loop, the antibody-urokinase complex displayed a greater rate of fibrinolysis than an equivalent amount of pure urokinase. However, therapeutic use of such complexes is unattractive due to the immunogenicity of murine monoclonal antibodies.

U.S. Pat. No. 4,564,596 discloses urokinase derivatives comprising urokinase covalently bonded to fibrinogen, either directly or through a specific aliphatic diamine. The derivatives are reported to have an increased affinity for fibrin and prolonged fibrinolytic effect. However, fibrinogen has procoagulant action, and may promote further development of thrombi. Thrombus-bound fibrinogen which is carrying urokinase will promote extension of the thrombus via either platelet aggregation or fibrin deposition, acting locally as a procoagulant agent. This may lead to reocclusion of the vessel.

Fibrinogen must be treated with thrombin, in order to maximize targeting to thrombi. Thus, the fibrinogen-urokinasae hybrid of U.S. Pat. No. 4,564,596 requires the presence of a thrombotic state for optimal performance. Moreover, fibrinogen is an adhesive protein, since it contains the amino acid sequence Arg-Gly-Asp. Fibrinogen binds to a variety of cells, providing a bridge between cells. Consequently, much of the injected fibrinogen-urokinase hybrid may bind to cells in the circulating blood, making less hybrid available to bind to thrombi.

Human fibrin fragment $E_1$ binds specifically to polymers of fibrin, Olexa et al., *Proc. Natl. Acad. Sci. USA* 77:1374-1378 (1980), and has the ability to bind to aged as well as fresh thrombi. Knight et al., *J. Clin. Invest.* 72:2007-2013 (1983). $^{123}$I-labeled fragment $E_1$ has been used to detect venous thrombi in patients. Knight et al., *Radiology* 156:509-514 (1985). In addition to fragment $E_1$, fragment $E_2$ and peptides having an amino acid sequence intermediate between fragments $E_1$ and $E_2$ may be labeled to detect thrombi, as disclosed in U.S. Pat. No. 4,427,646.

CNBr-digest fragments of fibrinogen have been shown to accelerate the activation of t-PA. Nieuwenhuizen et al, *Biochem. Biophys. Acta* 755:531-533 (1983); Lijnen et al, *Eur. J. Biochem.* 144:541-544 (1984); Nieuwenhuizen et al, *Biochem. Biophys. Acta* 748:86-92 (1983). However the fibrinogen fragments afford no protection from inactivation of t-PA by plasminogen activator inhibitors present in plasma.

What is needed is a thrombus-dissolving agent having more potent lytic activity than the known plasminogen activators, but without the disadvantages of such known activators. Ideally, a thrombolytic agent should have very high fibrin specificity, and should immobilize itself on or near the fibrin surface of a thrombus. It should activate only fibrin surface-bound plasminogen without activating circulating plasminogen. In addition, a lytic agent should have a very high potential for plasmin generation on a thrombus surface, and have a prolonged half-life time in the circulation so that lengthy, high-dose infusions are not necessary. The thrombolytic agent which has the potential to produce more plasmin from a given amount of plasminogen will perform as a better lytic agent, because the required amount of plasmin concentration on the thrombus surface can be achieved by using a smaller amount of activator units.

By "plasminogen activator" is meant any agent capable of activating the zymogen plasminogen to the fibrinolytic enzyme plasmin.

By "fibrin fragment" is meant any fragment resulting from the single or sequential plasmin cleavage of intact cross-linked or non-cross-linked fibrin ("native fibrin fragment"), and any such fragment which is further cleaved, derivatized or modified in any manner, while retaining a substantial portion of the native fragment amino acid sequence ("non-native fibrin fragment").

By the term "linked", as used herein in describing the union between a plasminogen activator and a fibrin fragment, is meant any form of chemical association or bond, including, but not limited to non-covalent complex formation, covalent bonding (including but not limited to covalent bonding by means of one or more cross-linking agents), and the like. Also included in the scope of such associations is the formation of a unitary protein by genetic engineering, resulting from the coexpression of genetic information for all or part of the fibrin fragment and plasminogen activator as a single protein.

SUMMARY OF THE INVENTION

A thrombolytic agent is provided comprising a fibrin fragment linked to a plasminogen activator. The fibrin fragment may be a native fragment of fibrin, or a non-native fragment. Native fragments of fibrin include, for example, fragments $E_1$, $E_2$, $E_3$, D and DD, and the (DD)E complex, which are obtained by plasmin degradation of cross-linked and/or non-cross-linked fibrin. Non-native fibrin fragments include, for example, smaller fragments of the native fragments, such as peptides having amino acid sequences intermediate between fragments $E_1$ and $E_2$. Non-native fibrin fragments further include modified, synthetic or derivatized native fragments. Covalent or non-covalent complexes of such native or non-native fibrin fragments are formed with a plasminogen activator such as t-PA, streptokinase, urokinase or scu-PA.

A thrombolytic composition is provided comprising a thrombolytic agent of the invention in an amount sufficient for thrombolysis, and a pharmaceutically acceptable carrier suitable for intravenous administration.

A method for dissolving vascular thrombi is provided by administering such compositions to a mammal.

DETAILED DESCRIPTION OF THE INVENTION

We have found that when a plasminogen activator is linked to a fibrin fragment, the resulting hybrid retains the ability of the parent fibrin fragment to bind fibrin clots (thrombi), and also retains the ability of the parent plasminogen activator molecule to convert plasminogen to its active enzyme form, plasmin. The fibrin fragment effectively serves as a vehicle for transporting the plasminogen activator directly to the thrombus surface. As a result, larger amounts of plasmin are generated in situ at the thrombus surface from the thus surface-bound plasminogen activator than from equivalent dosages of free plasminogen activator. Administration of the thrombolytic agents of the invention thus mimics local administration of plasminogen activator, which has been previously shown to be about five times more effective than systemically-infused plasminogen activator.

Because of the thrombus-targeting effect of the fibrin fragment component, the hybrids of the invention are more efficient thrombolytic agents than plasminogen activator alone. They produce more plasmin per amount of endogenous plasminogen than the corresponding uncomplexed plasminogen activator molecules. They also generate more plasmin from fibrin-surface bound plasminogen than the plasminogen activator molecule alone. Consequently, the dosage of plasminogen activator administered as a complex according to the invention may be reduced from the high levels of free plasminogen activator presently being administered in thrombolytic therapy. The hybrids generate therapeutically useful levels of plasmin at the thrombus site without significant systemic plasminogen activation. The frequency and duration of infusion of lytic agents of the invention is less than that required for free plasminogen activator.

Systemic activation of plasminogen results in excess plasmin generated in circulating blood. This causes degradation of fibrinogen, which results in lowering of platelet adhesion and aggregation. Excess circulating plasmin also degrades thrombospondin and other components of the hemostatic plug. These developments are indicative of a lytic state, which may give rise to bleeding complications when vascular lesions and pre-existing impaired hemostatic plugs are present. Pre-existing impaired hemostatic plugs are easily dissolved, which may lead to bleeding. Pre-existing vascular or epithelial defects may also become very vulnerable to bleeding. Moreover, heparin therapy in combination with conventional thrombolytic therapy facilitates the development of bleeding complications in dose and time-dependent manner.

The thrombolytic hybrids of the invention, because of the thrombus-targeting property of the fibrin fragment component, minimize excess circulating plasmin and the aforementioned complications. In addition, it is believed that the fibrin fragment component of the complex may exert some inhibitory effect on fresh fibrin formation or propagation of the formed thrombus. Use of the thrombolytic hybrids allows clinicians to substantially reduce the dosage of heparin, and significantly lower the risk of bleeding complications during thrombolytic therapy. It is believed that the thrombolytic hybrids of the invention are unlikely to cause significant bleeding episodes, based upon the known mechanism of hemorrhagic complications following thrombolytic therapy.

In contrast to the fibrinogen-urokinase hybrids of U.S. Pat. No. 4,564,596, the hybrids of the present invention are not procoagulant. Moreover, unlike the aforementioned prior art fibrinogen-containing hybrids, the hybrids of the invention do not bind avidly to platelets, and do not promote platelet aggregation. Thus, the instant thrombolytic hybrids do not promote reocclusion, which is primarily triggered by platelet aggregation and deposition.

The hybrids of the invention, being formed from fibrin fragments as opposed to fibrinogen, are smaller than the prior art fibrinogen-urokinase hybrids, and therefore are believed to exhibit better thrombus penetration. They do not require activation in the body by a thrombotic (or other) state for targeting to thrombi. Since the fibrin fragments either do not contain the Arg-Gly-Asp sequence, or contain a greatly reduced amount in comparison to fibrinogen, the hybrids of the invention should not bind appreciably to cell surface receptors. They may be administered at lower doses than that required for the fibrinogen-urokinase prior hybrids.

Plasma constitutes a hostile environment for exogenous plasminogen activator. Cellular components of the blood and the hepatocytes of the liver rapidly take up exogenous plasminogen activator from the circulation. In contrast to the short half-life of plasminogen activators in present use, the lytic hybrids of the invention are protected, by virtue of the fibrin fragment component, from the inhibitors normally present in plasma, and from rapid uptake by the liver. Consequently, the thrombolytic agents of the invention enjoy an increased half-life in the circulation in comparison to naked plasminogen activators.

The thrombolytic agents of the invention are formed by linking a plasminogen activator to a fibrin fragment. Plasminogen activators may be purified from natural materials, may be produced by cells grown in culture, or may be obtained by recombinant DNA technology. Plasminogen activators include, but are not limited to, streptokinase, urokinase, scu-PA, t-PA, and the like.

Plasminogen Activators

One class of plasminogen activators which may be linked to fibrin fragments according to the present invention includes products of bacterial origin, such as streptokinase. Also known as streptococcal fibrinolysin, streptokinase is a protein produced by hemolytic streptococci. The purification of streptokinase is described in one or more of the following U.S. patents, the complete disclosures of which are incorporated herein by reference: U.S. Pat. Nos. 3,063,913; 3,063,914; 3,138,452; 3,276,304; 3,016,337; 3;042,586; and 3,107,203.

Another class of plasminogen activators which may be linked to fibrin fragments according to the invention includes any of the various plasminogen activators distributed throughout mammalian urine, blood or tissue. The two major groups include urokinase-type plasminogen activators, and non-urokinase-type plasminogen activators.

The prototype urokinase-type plasminogen activator, urokinase, is formed in kidney tissue and excreted into urine. Several tissues and tumors in tissue culture produce urokinase or a urokinase-type plasminogen activator. Urokinase is typically isolated from e.g., human urine or from tissue culture of kidney cells, or is obtained by genetic engineering. It may be isolated from human male urine according to one or more of the following U.S. patents, the entire disclosures of which are incorporated herein by reference: U.S. Pat. Nos. 2,961,382; 2,989,440; 2,983,647; and 3,081,236. Also see White et al., *Biochemistry* 5:2160 (1966). More recent processes for isolation of urokinase are disclosed in the following U.S. patents, the entire disclosures of which are incorporated herein by reference: U.S. Pat. No. Re. 29,980, directed to a method for obtaining urokinase directly from human urine comprising contacting urine with an acrylonitrile polymer of specific porous structure; U.S. Pat. No. 4,259,447, utilizing absorption with a porous solid matrix of specific surface area on which a protein is immobilized; U.S. Pat. Nos. 4,537,852; 4,259,448; 4,190,708; 3,957,582; 3,930,945; 3,930,944; and 3,884,760.

There are three forms of native urokinase, all having catalytic activity to convert plasminogen to plasmin. The most intact is single-chain urokinase (scu-PA) which is also called "prourokinase" (54 kDa molecular weight). Plasmin cleaves this molecule without a change in total molecular weight to form "two-chain urokinase", (typically referred to simply as "urokinase"). The latter comprises an about 22 kDa light chain linked to an about 32 kDa heavy chain by a disulfide bond. The heavy chain contains the enzyme active site. Long plasmin digestion of this 54 kDa high molecular weight urokinase form produces a low molecular weight form of urokinase. The latter contains two chains, one chain being approximately 32 kDa and the other being approximately 2 kDa. The 32 kDa chain corresponds to the heavy chain of high molecular weight urokinase. The two urokinase types do not differ significantly in in vitro enzymatic activity.

The present invention contemplates the linkage of any of the various urokinase-type plasminogen activators to fibrin fragments to produce thrombus-targeted fibrinolytic hybrids.

In addition to native urokinase-type plasminogen activators, the present invention contemplates the linkage of any modified urokinase-type plasminogen activator to a fibrin fragment. One such modified urokinase-type molecule is obtained by coupling urokinase to polyalkylene glycol (molecular weight 200–20,000) as described in U.S. Pat. No. 4,640,835, incorporated herein by reference. Other known urokinase derivatives suitable for therapeutic purposes include, for example, complexes of urokinase with heparin or dextran sulphate, and urokinase derivatives wherein the carbohydrate structure of the native urokinase molecule is modified to produce a longer-acting thrombolytic agent. Such carbohydrate-modified urokinases are disclosed, for example, in U.S. Pat. No. 4,326,033, which is incorporated herein by reference.

Non-urokinase plasminogen activators are produced by human uterine tissue, as well as by certain tumor cells in culture. A subclass of non-urokinase plasminogen activators known as "vascular" plasminogen activators (hereinafter collectively "tissue plasminogen activator" or "t-PA"), appear to be produced by the human blood vessel wall. These molecules activate plasminogen upon a fibrin surface, whereas the urokinase-type plasminogen activators do not require a fibrin clot network to activate plasminogen to plasmin.

Tissue plasminogen activator ("t-PA") exists in a form including a single protein chain ("one-chain t-PA"), and a two protein chain form ("two-chain t-PA"). The latter is proteolytically derived from the one-chain molecule. It is theorized that the two-chain protein is associated with produced fibrin and that proteolytic conversion from the one-chain to the two-chain material occurs at the locus of the conversion of plasminogen to plasmin. Both forms may be utilized in the practice of the invention.

Tissue plasminogen activator may be obtained from culture fluid of human or mammalian tissues such as uterus, kidney, lung, and small intestine. Normal or tumor cells are employed. Preparation of t-PA from various cultured normal human cells is disclosed in the following U.S. patents, which are incorporated herein by reference: U.S. Pat. Nos. 4,335,215; 4,505,893; 4,537,860; and 4,550,080. Production of t-PA from normal human embryonic lung cells is described by Rijken et al., *J. Biol. Chem.* 256(13):7035–7041 (1981), incorporated herein by reference. Pohl et al., *FEBS Lett.*

168(1):29-32 (1984), incorporated herein by reference, discloses production of t-PA from human uterine tissue.

Tissue plasminogen activator may also be obtained from tumor cells. For example, t-PA has been prepared from Bowes melanoma cells in culture according to Rijken et al., supra, and published European Patent Application 41,766 (1981), incorporated herein by reference. The Bowes cell t-PA is a glycoprotein of about 68-70 kDa molecular weight and 527 amino acids. It contains an A-chain and a B-chain. Two variants, known as types I and II, differ in the A-chain by about 2-3 kDa. Ranby et al., FEBS Lett. 146(2):289-292 (1982); Wallen et al., Eur. J. Biochem. 132:681-686 (1983). The protein moiety of the melanoma tissue plasminogen activator has been cloned and expressed in E. coli. See published British Patent Application 2,119,804; Pennica et al., Nature 301:214-221 (1983). Recombinant t-PA produced by expressing Bowes melanoma genes in cultured mammalian cells has been used in therapy. U.S. Pat. No. 4,661,453, incorporated herein by reference, discloses t-PA obtained from prostate adenocarcinoma cells.

Recombinant t-PA is disclosed in U.S. Pat. No. 4,766,075, incorporated herein by reference.

While recombinant t-PA derived from E. coli is non-glycosylated, and contains only the protein moiety of t-PA, the present invention contemplates the use of either glycosylated or non-glycosylated t-PA to form the thrombus-targeted hybrids of the invention. Glycosylated t-PA may be obtained from non-human sources such as Chinese hamster ovary cells according to published European Patent Application 117,059 (1984) and Kaufman et al., Mol. Cell. Biol. 5:1750-1759 (1985), and from mouse L cells according to Browne et al., Gene 33:279-284 (1985), all incorporated herein by reference. Glycosylated t-PA may be produced by recombinant DNA techniques according to Zamarron et al., J. Biol. Chem. 259(4):2080-2803 (1984) and Collen et al., J. Pharmacol. Expertl. Therap. 231(1):146-152 (1984), incorporated herein by reference. Published European Patent Applications 143,081 (1985) and 174,835 (1986) disclose the expression of t-PA in yeast by recombinant techniques, while published European Patent Application 178,105 (1986) discloses a glycosylated uterine t-PA expressed in mouse or yeast cells. The aforesaid European patent applications are incorporated herein by reference. U.S. Pat. No. 4,751,084 discloses glycosylated t-PA from normal human colon fibroblast cell line CCD-18Co, ATCC CRL-1459.

These and other native and modified t-PA molecules known to those skilled in the art have utility in the practice of the present invention.

Also useful in the practice of the invention is the plasminogen activator known as "angiokinase", the purification of which from highly vascularized connective tissue of mammals is disclosed in U.S. Pat. No. 4,532,129, incorporated herein by reference.

While any plasminogen activator may be employed in the practice of the invention t-PA and scu-PA are preferred, owing to their superior thrombus specificity.

Native Fibrin Fragments

Fibrin is formed by cleavage of its precursor, the soluble plasma protein fibrinogen, by the action of thrombin. Fibrin forms the clot matrix which is cross-linked by Factor XIIIa to form a stabilized clot. Human cross-linked fibrin is degraded by plasmin, thereby releasing characteristic degradation products: (DD)E complex, fragment DD, fragment E and alpha polymer remnants. The (DD)E complex contains fragment $E_1$ and fragment DD. The (DD)E complex is susceptible to further degradation by plasmin resulting in cleavage of fragment $E_1$ to fragment $E_2$ without loss of the ability to bind fragment DD. Digestion of fragment $E_2$ to $E_3$ results in dissociation of the complex. The terminal plasmin degradation products of cross-linked fibrin are therefore fragments DD and $E_3$. The complete reaction scheme is thus: fibrin→(DD)$E_1$→(DD)$E_2$→DD+$E_3$.

The fibrin fragments which may be linked to a plasminogen activator to form the thrombus-targeted complexes of the invention may be obtained by cleavage of cross-linked or non-cross-linked fibrin. Such fragments have affinity for fibrin and/or protect the plasminogen activator to which they are bound from inactivation in plasma. The fibrin fragments also enhance the activity of the plasminogen activator molecule. They may also exert an inhibitory effect on fresh fibrin formation or propagation of the formed thrombus. Fragments $E_1$, $E_2$ and DD, and (DD)E complex are particularly useful for binding with t-PA or scu-PA to form thrombolytic complexes.

Native fibrin fragments useful in the practice of the present invention include, for example, fragments $E_1$, $E_2$, $E_3$, D and DD, and the (DD)E complex. The various plasmin degradation products of fibrin, and their preparation, is reported in Olexa et al., Biochemistry 18:991 (1979) and J. Biol. Chem. 254:4925 (1979), both of which are incorporated herein by reference.

The E fragments comprise the plasmic cleavage products of human cross-linked fibrin. They contain the NH$_2$-terminal regions of all six polypeptide chains of fibrin. The amino acid sequences of the various fragments E have been established. Olexa et al., Biochemistry 21:6139-6145 (1981). At least three species of fragment E have been isolated and characterized, namely fragments $E_1$, $E_2$ and $E_3$, having molecular weights of about 60 kDa, 55 kDa and 50 kDa, respectively. These species are sequential degradation products. Microheterogeneity of each species has been noted. Fragments $E_1$ and $E_2$, and peptides having an amino acid sequence intermediate between fragments $E_1$ and $E_2$, have affinity for preformed clots as disclosed in U.S. Pat. No. 4,427,646. Each such peptide is useful in forming thrombus-targeting fibrinolytic hybrids.

Fragment $E_1$ is particularly useful as a thrombus-targeting vehicle for plasminogen activators. Fragment $E_1$ specifically binds to polymers of fibrin, Olexa et al., Proc. Natl. Acad. Sci. USA 77:1374-1378 (1980). It has the advantage of lower likelihood of antigenicity than the murine monoclonal antibodies used in the prior art, because it is a fragment of a native human protein. Moreover, fragment $E_1$ has been shown to have the ability to bind to aged as well as fresh thrombi. Knight et al., J. Clin. Invest. 72:2007-2013 (1983). The binding of fragment $E_1$ to thrombi in patients with documented venous thrombosis, Knight et al., Radiology 156:509-514 (1985), demonstrates the usefulness of this fragment as a molecular marker for specifically targeting thrombi in vivo.

The basic process for the preparation of the various native plasmin degradation products of fibrin, as described in U.S. Pat. No. 4,427,646, is as follows. A fibrin clot from fibrinogen enriched with Factor XIII is formed. The clot is hydrolyzed with plasmin and the resulting digest is centrifuged to remove large clot particles. The supernatant contains soluble degradation products, which are separated according to molecular weight, preferably on an agarose gel bead column, to give the (DD)E complex. Fragments $E_1$ and $E_2$ may be obtained from the purified (DD)E complex by incubation in a concentrated salt solution to cause dissociation of fragment DD and fragments $E_1$ and $E_2$, followed by separation according to molecular weight, preferably by means of an agarose gel bead column.

Fragment DD, a dimeric degradation product of fibrin, is capable of binding to fibrin polymers and fibrin monomers but does not bind fibrinogen. It is more resistant to plasmic degradation than fragment $E_1$, Olexa et al, *J Biol. Chem.* 254:4925–4932 (1979), and because of its larger size may offer greater protection of the plasminogen activator and a longer residence time in the blood than Fragment $E_1$.

The fragments generally known as "fragment D" comprise a group of fibrinogen or fibrin derivatives characterized by the same immunologic reaction and similar three-chain structure. They are monomeric plasmic degradation products of fibrinogen, which are also obtained by plasmin cleavage of non-cross-linked fibrin. They bind to a site available on fibrin monomer, but not available on fibrinogen. Fragment $D_1$ has the highest molecular weight (100 kDa) of the various D fragments. As used herein, unless otherwise noted, "fragment D" means any of the various D fragments, such as $D_1$, $D_2$ and $D_3$.

While the (DD)E complex does not bind to fibrin, it is believed that this complex nevertheless offers a protective effect to the plasminogen activator such that the latter may be transported safely to a thrombus. It is further believed that the affinity of certain plasminogen activators, such as t-PA, for the fibrin deposit in a thrombus will be higher than the affinity of the plasminogen activator for any of these fragments, so that the activator will dissociate from the carrier fragment in the vicinity of the thrombus and bind to the fibrin to activate plasminogen on the surface of the thrombus. Moreover, while (DD)E complex does not bind fibrin, it has a potentiating effect on the lytic activity of the plasminogen activators. Thus, the (DD)E complex may be efficiently used as a shield for the protection of the plasminogen activator molecule and therefore enhance the activity of the plasminogen activator molecule.

It should be noted that while the native fibrin fragments $E_1$, $E_2$, $E_3$, DD and (DD)E are obtained through degradation of cross-linked fibrin, fragment D is obtained from non-cross-linked fibrin. Fragment D may also be obtained as a monomeric plasmic degradation product of fibrinogen.

The preparation of fibrin for the generation of fibrin fragments, and for the preparation of a fibrin-diatomaceous earth affinity matrix utilized in the purification of fibrin fragments and/or fibrinolytic complexes, is described as follows.

Preparation of Fibrin

Sonicated human cross-linked fibrin may be prepared from plasminogen- and thrombin-free human fibrinogen according to Lukas et al, *J. Biol. Chem.* 258:4249–4256 (1983), incorporated herein by reference. Briefly, purified fibrinogen is clotted with thrombin at a ratio of one unit per mg of fibrinogen in the presence of calcium ions. The fibrin clot is then exposed to sonication in an appropriate cell disrupter (e.g. from Heat Systems-Ultrasonics, Plainview, N.Y.) with ice cooling.

Preparation of Non Cross-Linked And Cross-Linked Fibrin-Diatomaceous Earth

Fibrin-diatomaceous earth comprises a fibrin clot immobilized on diatomaceous earth particles, which serve as nuclei for small fibrin clot assemblies. The non-cross-linked and cross-linked fibrin-diatomaceous earth utilized as an affinity matrix material in the following procedure may be prepared as follows:

Non-cross-linked fibrin-diatomaceous earth is prepared essentially as described by Husain et al., *Proc. Natl. Acad. Sci. USA* 78:4265–4269 (1981), with the following modifications. After removing fine particles from the starting diatomaceous earth (Hyflo Super Cel, Fluka Chemical Corp., Ronkonkoma, N.Y.) by repeated suspension in water, the diatomaceous earth material is washed twice, each time by gently stirring with one liter of 1M NaCl for two hours. This treatment removes material present in some batches of diatomaceous earth that would otherwise retard clotting of the fibrinogen. To obtain fibrin-diatomaceous earth, plasminogen-free fibrinogen is clotted by thrombin in the presence of diatomaceous earth and then washed on a Buchner funnel with 0.05M Tris-HCl buffer, containing 0.15M NaCl, pH 7.4. Fibrin clots which form become incorporated into the particles. Residual thrombin is inhibited by D-Phe-Pro-Arg-chloromethylketone (Calbiochem-Behring Corp., San Diego, Calif.). Cross-linked fibrin-diatomaceous earth is prepared by suspending washed, non-cross-linked fibrin-diatomaceous earth in Tris buffer, containing 5 mM $CaCl_2$ and 1M mercaptoethanol, and incubating the suspension at 20° C. for 15 hours. The cross-linked fibrin-diatomaceous earth is subsequently washed in a column. Sodium dodecylsulfate polyacrylamide gel electrophoresis ("SDS-PAGE") may be used to show complete cross-linking of the alpha and gamma fibrin chains.

The preparation and characterization of certain pure, homogeneous soluble fibrin fragments is illustrated as follows.

Preparation Of (DD)E Complex (DD)E complex may be prepared from purified human cross-linked fibrin as described in Olexa et al, *Biochemistry* 18:991–995 (1979). Accordingly, 1 g of dry cross-linked fibrin and 1 CTA unit of plasmin (1 CTA unit/1 g fibrin; Kabi, Stockholm, Sweden) are suspended together as quickly as possible in 20 ml of pre-warmed 0.15M Tris-HCl buffer containing 5 mM $CaCl_2$ and 0.02% sodium azide, pH 7.4. (A "CTA unit" is the Committee on Thrombolytic Agents standard unit which defines the proteolytic activity of plasmin by its action on a casein substrate.) The digestion is carried out under constant gentle stirring at 37° C. for strictly 21.5 hours for maximum yield of (DD)E complex. The digestion is then stopped by addition of 0.01 ml of aprotinin (Trasylol ®, Bayer & Co.) to a final concentration of 100 KIU/1 CTA unit of plasmin. (The potency of aprotinin as an enzyme inhibitor is calibrated according to the amount of kallikrein it can inhibit. Hence its activity is expressed in units of kallikrein inhibitor units per ml or "KIU/ml".) The digest is stored frozen and control SDS-PAGE and alkaline-PAGE are performed. The small amount of particulate material is removed by centrifugation at 3,000 g for 15 minute at 4° C. The digest supernatant is then chromatographed on a Sepharose ® CL-6B column (Pharmacia, Piscataway, N.J.; 2.5×190 cm) equilibrated and eluted with 0.05M Tris-HCl buffer containing 0.1M sodium chloride, 0.028M sodium citrate, 25 KIU/ml of aprotinin and 0.02% sodium azide, pH 7.4. (Sepharose ® CL is highly purified agarose which has been treated with dibromopropanol.) Approximately 200-250 mg of protein in a volume of 10-15 ml is applied in each run and the flow rate is adjusted to about 40-45 ml/hour. Fractions of 8 ml within main peaks are combined and concentrated and subsequently analyzed on SDS-PAGE and alkaline-PAGE. The main (second) peak fractions contain pure homogeneous (DD)E complex. The preparation is concentrated by ultrafiltration and pooled.

Preparation Of Fragment DD

Fragment DD is prepared in a similar manner but with a different proportion of plasmin to dry fibrin. To achieve a maximum yield of fragment DD, 1 g of dry cross-linked fibrin is digested by 10 CTA units of plasmin (10 CTA units/1 g fibrin) for strictly 21.5 hrs. Then digestion is terminated by 10 ml (100 KIU/1 CTA unit of plasmin) of aprotinin and the reaction mixture is stored frozen until control SDS-PAGE is performed. The digest is then centrifuged at 3000 g for 15 minutes at 4° C. and the supernate is then chromatographed on the same type of column as used in the above-identified (DD)E complex preparation, equilibrated and run by the same buffer system as above, but with a higher molar concentration of sodium chloride (1M NaCl), pH 7.4. The fractions (8 ml) within the main peak are combined and analyzed on SDS-PAGE. The main peak fractions contain relatively pure and homogeneous fragment DD. The sample is concentrated and pooled. It is observed that the tail of the main peak also contains a significant amount of fragment DD with traces of impurities of fragments $D_1$ and $E_3$. These fractions are purified on an anti-E affinity column (Anti-E Sepharose ®) and run through a fibrin-diatomaceous earth affinity column to pool the fragment with total preservation of binding affinity for fibrin.

Preparation of Fragments $E_1$ and $E_2$

About 50 mg of (DD)E complex is dissociated with 3M urea, pH 5.5 for 1 hr at 37° C. The resulting species comprise denatured fragment DD and native and functionally active fragment $E_1$. The sample is then chromatographed on a Sepharose ® CL-6B (0.9×90 cm) column, equilibrated and eluted with the same buffer system as employed in the fragment DD separation. Denatured fragment DD and fragments E ($E_1$ and/or $E_2$) elute in two markedly separated peaks. Control SDS-PAGE is performed. Fragments E are concentrated and pooled. The preparation contains about 25% fragment $E_2$ and 75% fragment $E_1$. The E species are separated by fast liquid protein chromatography ("FPLC") on a Mono-Q ® HR5/5 ion exchange column (5 mm×5 cm glass column packed with 1 ml of Mono Q ® anion exchange resin; ion capacity=0.27−0.37 Cl−. Mono Q ® anion exchange resin comprises the relatively strong anionic exchanger function, —$CH_2N^+(CH_3)_3$, on a base of monodisperse hydrophilic polymer particles. Negatively charged species are bound through the quaternary amine groups, which remain positively charged over the pH range 2-12. Affinity chromatography on fibrin-diatomaceous earth is then performed to isolate functionally intact fragment $E_1$.

Preparation of Fragment $E_3$

Fragment $E_3$ is obtained from a terminal plasmic digest of cross-linked fibrin by column gel filtration according to Olexa et al, *Biochemistry* 18:911-995 (1979). Accordingly, cross-linked fibrin is digested by 100 CTA units plasmin/1 g fibrin for 24 hours and then gel-filtered on a Sepharose ® CL-6B column as for fragment DD. Fragment $E_3$, the second peak, is separated from fragment DD and alpha polymer remnant present in the first and third peaks, respectively. The purity and homogeneity of the fragment are tested on SDS-PAGE. The fractions are pooled, then concentrated by ultrafiltration and subsequently purified on an anti-E affinity column.

Preparation of Fragment D

Fragment $D_1$ is prepared by a prolonged plasmic digestion of non-cross-linked fibrin in the presence of 25 mM $CaCl_2$ and purified by Pevikon block preparative electrophoresis according to Marder et al, *Throms. Diath. Haemorrh.* 22 234-239 (1969), incorporated herein by reference. A mixture of fragments $D_2$ and $D_3$ is obtained from this procedure in the absence of 25 mM $CaCl_2$.

Non-Native Fibrin Fragments

As an alternative to native fibrin fragments, non-native fibrin fragments may be linked to an appropriate plasminogen activator to form thrombus-targeting fibrinolytic hybrids. Such non-native fibrin fragments include modified plasmin degradation fibrin fragments, such as heat-denatured, CNBr-modified or acid-denatured fragments; synthetic fragments, i.e., synthetic peptides having the same sequence as a portion of or all of the amino acid sequence of the corresponding naturally-occurring fibrin fragment, or synthetic peptides with one or more amino acids replaced, such synthetic peptides comprising single chains or chains linked together by disulfide or other chemical bonds; and derivatized fragments, that is, native fibrin fragments which have been reacted with or treated with one or more chemical agents.

Synthetic peptides containing a portion of the native fibrin fragment are also useful in the practice of the invention. One such fragment is the $gamma_{391}$-$gamma_{405}$ fragment described by Cierniewski et al, *J. Biol. Chem.* 262:13896-13901 (1987), incorporated herein by reference. Other synthetic peptides comprising portions of native fibrin degradation fragments are known to those skilled in the art.

Derivatized fragments may be formed by reacting a fibrin fragment with, e.g. methyl iodide, acylating agents, carbohydrates, carbodiimides, etc. which may be used to facilitate alteration of one or more properties, such as prolongation of biological half-life.

Derivatization may also include blockage of the plasminogen binding site on the fibrin fragment with an appropriate blocking agent. Some fibrin degradation products retain intact binding sites for plasminogen. Hybrids formed from such fragments could theoretically bind plasminogen from the systemic circulation and generate plasmin in the circulating blood before immobilizing on a clot surface. This may lead to undesirable fibrinogenolytic activity in the circulation. To prevent this, the plasminogen binding site on the fibrin fragment is blocked.

Blockage of the plasminogen binding site may be accomplished in several ways. Inactive plasmin derivatives may be prepared by treating plasmin with, e.g., diisopropyl fluorophosphate, or other plasmin-inactivating agent. Such inactivated plasmin derivatives may be non-covalently bound to a fibrin fragment to block the fragment's plasminogen binding site. According to one method, plasmin molecules are inactivated by inhibitors such as phenylmethylsulfonyl fluoride ("PMSF") and diisopropyl fluorophosphate ("DFP"). The inhibitors inactivate the plasmin molecule's enzyme active site. These inactivated plasmin molecules are then used to saturate the fibrin fragment. The deactivated plasmin molecules, which bind to the fibrin fragment via their fibrin-binding function, may thus block all the plasminogen-binding sites on the fibrin fragment. The plasmin molecules so bound will not express their enzyme activity due to their prior inactivation with inhibitor.

Alternatively, the fibrin fragment's plasminogen binding site may be blocked by covalently attaching inactivated plasminogen derivatives to the fibrin fragment by specific cross-linking reagents. Inactivated plasmin is coupled through its active enzyme site to the fibrin fragment's plasminogen binding site by means of the cross-linking agent. Examples of suitable heterobifunctional cross-linking reagents for this purpose are those reagents which carry a PMSF moiety as one functional group and an aromatic azido residue as the other functional group. The PMSF moiety binds covalently with the active site of the plasmin molecule, while the azido group will couple the plasmin molecule to the plasminogen binding site of the fibrin fragment portion of the fibrinolytic hybrid. One such heterobifunctional agent believed suitable for this purpose is:

Another approach to prevent plasminogen binding to the fibrin fragment portion of the fibrinolytic hybrid utilizes isolated plasminogen kringles as a blocking agent to saturate the fibrin fragment's plasminogen binding site. Kringles comprise a class of disulfide-bridged, triple loop structures existing as independent, autonomous folding domains in a number of proteins. Kringles have been found to exist in, for example, scu-PA (kringle 1), t-PA (kringle 2) and plasminogen (kringles 4 and 5). Plasminogen may be cleaved between kringle 4 and kringle 5 by 100 mM elastase. Machovich et al., *Circulation* 78(4), Supplement 11, Abstract No. 2039 of "Abstracts of the 61st Scientific Session of the American Heart Association". Synthesis of isolated plasminogen kringles is possible by recombinant DNA technology. The kringles may be combined with the fibrinolytic hybrids of the invention and irreversibly cross-linked so as to be indifferent to circulating plasminogen molecules.

The various native and non-native fibrin fragments which find utility in the present invention may be prepared by appropriate enzyme digest of the parent molecule fibrin. It is also contemplated that fibrin fragments, which may be linked to plasminogen activator molecules to form fibrinolytic hybrids according to the invention, may be prepared by genetic engineering techniques known to those skilled in the art.

Preparation of Plasminogen Activator-Fibrin Fragment Fibrinolytic Complexes

Non-covalent fibrinolytic complexes may be prepared between fibrin fragments and plasminogen activator molecules which have inherent binding affinity between them. Exemplary complexes include, but are not limited to, complexes of fragments $E_1$, $E_2$, D and DD, and (DD)E complex linked to t-PA or scu-PA. Other non-covalent complexes may be prepared provided the fibrin fragment and plasminogen activator molecule have an inherent binding affinity between them.

The non-covalent complexes of the present invention are prepared by incubating a fibrin fragment with a plasminogen activator molecule in a molar ratio favoring complex formation, under conditions favoring stabilization of the resulting complex. Generally, a reaction vessel is pre-coated with serum albumin. An amount of plasminogen activator molecule, depending upon the required activity, is incubated with about a 1 to about 1000-fold, preferably about 10 to about 1000-fold, molar excess of fibrin fragment at, e.g., 37° C. for thirty minutes. Following incubation, human serum albumin and/or other stabilizer and 1-2 mM $CaCl_2$ are added to the mixture. Such other stabilizers include, for example, non-ionic detergents, 0.01%-0.1% concentration. Such detergents include, for example, polysorbate 80 (Tween ® 80) and polysorbate 20 (Tween ® 20). Formation of complexes is verified by non-dissociating PAGE. The complexes are then purified by FPLC. They may then be tested for intactness of fibrin binding affinity and plasminogen activating activity. The functional activity of the complexes may then be calibrated by standard chromogenic substrate assay or other suitable functional assay. The chromogenic plasmin substrate H-D-Val-Leu-Lys-p-nitroaniline (S-2251) may be used for this purpose.

Thrombolytic hybrids may also be formed by covalently coupling the fibrin fragment to a plasminogen activator. The components may be covalently cross-linked by appropriate homobifunctional or heterobifunctional cross-linking agents.

The covalently cross-linked fibrinolytic hybrids of the present invention may be prepared by utilizing homobifunctional cross-linking reagents, e.g. disuccinimidyl tartrate, disuccinimidyl suberate, ethylene glycolbis(succinimidyl succinate), 1,5-difluoro-2,4-dinitrobenzene ("DFDNB"), 4,4'-diisothiocyano-2,2'-disulfonic acid stilbene ("DIDS"), and bismaleimidohexane ("BMH"). The cross-linking reaction occurs randomly between the fibrin fragment and plasminogen activator.

Alternatively, heterobifunctional cross-linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl-)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl-)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sulfo-SMPB"), bromoacetyl-p-aminobenzoyl-N-hydroxy-succinimidyl ester, iodoacetyl-N-hydroxysuccinimidyl ester, and the like.

For heterobifunctional cross-linking, the fibrin fragment is derivatized with, e.g., the N-hydroxysuccinimidyl portion of the bifunctional reagent, and the derivatized fibrin fragment is purified by gel filtration. Next, plasminogen activator is reacted with the second functional group of the bifunctional reagent, assuring a directed sequence of binding between components of the fibrinolytic hybrid.

Typical heterobifunctional cross-linking agents for forming protein-protein conjugates have an amino reactive N-hydroxy-succinimide ester as one functional group and a sulfhydryl reactive group as the other functional group. First, epsilon-amino groups of surface lysine residues of the fibrin fragment are acylated with the NHS-ester group of the cross-linking agent. The plasminogen activator molecule, possessing free sulfhydryl groups, is reacted with the sulfhydryl reactive group of the cross-linking agent to form a covalently cross-linked fibrinolytic hybrid. Common thiol reactive groups include maleimides, pyridyl disulfides, and active halogens. For example, MBS contains a N-hydroxy-succinimide ester as the amino reactive group, and a maleimide moiety as the sulfhydryl reactive group.

Photoactive heterobifunctional cross-linking reagents, e.g. photoreactive phenyl azides, may also be employed. One such reagent, SASD, may be linked to the fibrin fragment via its N-hydroxysuccinimidyl ester group. The conjugation reaction is carried out at pH 7 at room temperature for about 10 minutes. Molar ratios between about 1 and about 20 of the cross-linking agent to fibrin fragment are used. Low ratios are favored in order to minimize chemical modification of binding sites on the fibrin fragments. The fibrin fragment to which cross-linking agent has been bound is then purified in the dark from reaction by-products by column gel filtration, e.g. polyacrylamide column filtration. Polyacryamide gel materials for gel filtration chromatography, consisting of porous polyacrylamide beads, are available, for example, as BioGel TM beads from Bio-Rad Corp., Richmond, Calif. The gels are available with a range of pore sizes, indicated by a suffix (P-2, P-4, P-6, etc.). The suffix corresponds to the smallest molecule which is completely excluded from the pores. For purifying fibrin fragments, a gel with pore sizes excluding 2 kDa and larger molecules is utilized, e.g., BioGel TM P-2 (1×10 cm column).

The purified, functionalized fibrin fragment is collected by affinity chromatography using a matrix having affinity for fibrin fragments, e.g., a fibrin-diatomaceous earth (1.5 ml) affinity column. Immobilized fibrin with the functionalized fibrin fragment bound thereto is then removed from the column and suspended in a solution of an appropriate plasminogen activator. An ultra-violet light source (e.g. Mineralight UVSL-25, Ultra Violet Products, Inc., San Gabriel, Calif.) is positioned 1 cm from the gently stirred suspension and irradiated in a long-wavelength range for about 10 minutes. The suspension is put back into the fibrin-diatomaceous earth column and washed with a buffer containing 0.15M NaCl, 0.1% bovine serum albumin, 0.01% polysorbate 80 and 25 KIU/ml of aprotinin to remove reaction byproducts. The covalently cross-linked fibrinolytic hybrid is eluted with the same buffer system containing 0.5M arginine. The complex is then separated from arginine by BioGel TM P-2 column chromatography.

Alternatively, conjugation of the fibrin fragment to the plasminogen activator may be accomplished by first derivatizing the plasminogen activator molecule. The plasminogen activator molecule is conjugated with, e.g. SASD as above, and the functionalized plasminogen activator molecule is purified as above by fibrin-diatomaceous earth affinity chromatography. Benzamidine-agarose chromatography may be substituted for fibrin-diatomaceous earth chromatography.

Benzamidine binds specifically to certain plasminogen activators such as t-PA and urokinase, which contain a benzamidine binding site. An affinity column for purifying plasminogen activators may thus be prepared by immobilizing benzamidine on a suitable matrix, e.g., highly purified agarose (Sepharose ®, Pharmacia Fine Chemicals, Uppsala, Sweden), particularly, agarose which has been treated with dibromopropanol (Sepharose ® CL-6B). Benzamidine-agarose is available from Pharmacia Fine Chemicals (Uppsala, Sweden) as a preswollen affinity gel in 0.9M NaCl, containing 0.01% merthiolate.

Following reaction with fibrin fragment under ultra-violet irradiation, and chromatography of the reaction mixture as above, the covalently cross-linked fibrinolytic hybrid is eluted with either 0.5M arginine in the case of fibrin-diatomaceous earth chromatography or 0.1M acetate, 0.4M NaCl, pH 4.0, in the case of benzamidine-agarose chromatography. When fibrin-diatomaceous earth is employed as the affinity matrix, the covalent complexes are further purified by BioGel TM P-2 chromatography, whereas if benzamidine-agarose chromatography is employed, the eluate is simply quickly neutralized.

While the above-described procedure utilizes SASD, a cleavable cross-linker, non-cleavable cross-linking reagents may be utilized which contain, e.g. alpha-hexanoate, rather than beta-ethyl-1,3-dithiopropopionate moieties. MSB is one example of a non-cleavable cross-linking reagent.

Figure 1:
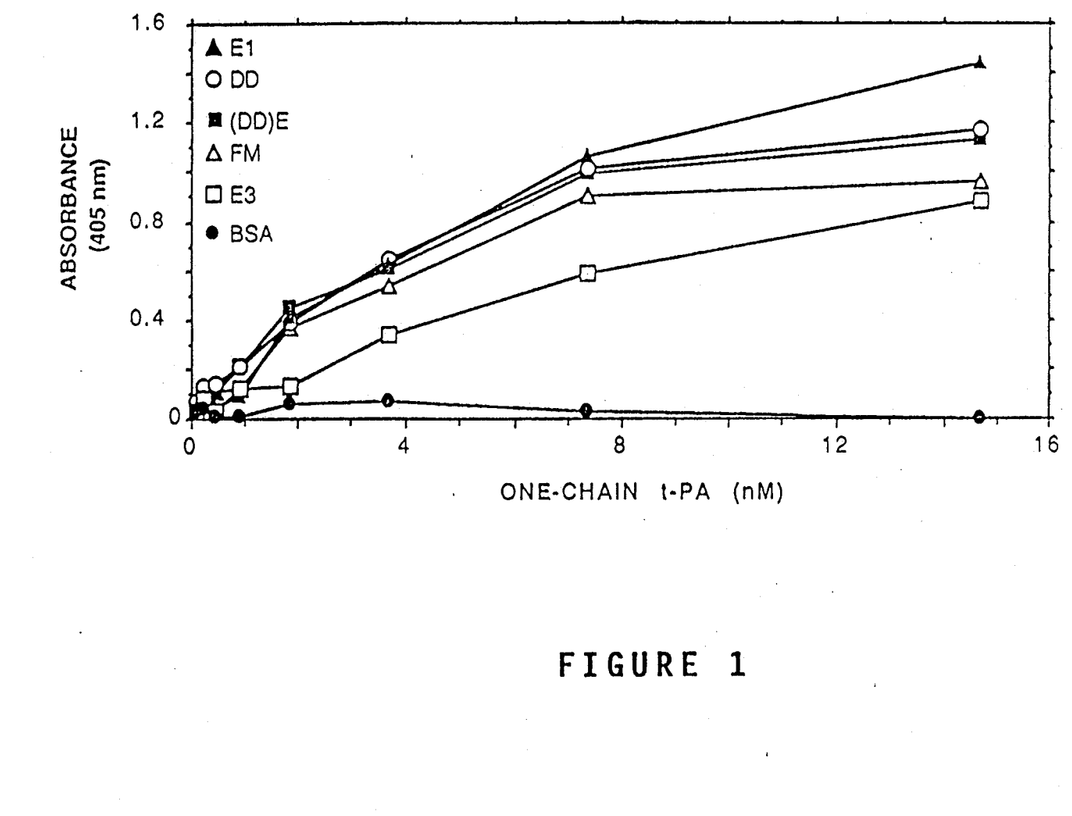
FIG. 1 is a plot of the binding of various concentrations of one-chain t-PA to fibrin monomer (FM), (DD)E complex, fragment DD or fragment $E_1$. The amount of t-PA bound to microtiter plates coated with fibrin monomer or fibrin fragments was determined by enzyme-linked immunosorbent assay ("ELISA"), measuring absorbance at 405 nm. The plates were coated with bovine serum albumin ("BSA") as a negative control.

The ability of fibrin fragments to form non-covalent complexes with plasminogen activators is demonstrated as follows. Fibrin monomer (FM), (DD)E complex, and fragments DD and $E_1$ were absorbed to the wells of Immulon C microtiter plates (Dynatech Laboratories, Chantilly, Virg.). Unoccupied binding surfaces were blocked by BSA. One-chain t-PA purified from a human melanoma cell line (American Diagnostica, NY, N.Y.) was added to the plates in incremental amounts from 0.1 to 15 nM concentration range and incubated for 3 hours. The amount of t-PA bound to the fibrin fragments on the plate was quantified by ELISA. Complex formation was evident throughout the entire range of t-PA concentration tested and was similar for fibrin monomer (FM), (DD)E complex, fragment DD and fragment $E_1$ (FIG. 1). Specificity of binding was confirmed by the lack of t-PA binding to BSA. These results demonstrate that t-PA forms non-covalent complexes with fibrin fragments.

Non-covalent complexes of plasminogen activators and fibrin fragments may be prepared according to the following non-limiting example:

EXAMPLE 1

Fragment DD/t-PA Non-Covalent Complex

A reaction vessel is pre-coated with 10 mg/ml solution of serum albumin and dried. Fragment DD (640 nmoles) is incubated with one-chain t-PA (3.2 nmoles, American Diagnostica, NY, N.Y.) in the albumin pre-coated vessel for ½ hour at 37° C. in the presence of 2 mM $Ca^{++}$. Ten milligrams of serum albumin and ten microliters of 10% solution of polysorbate 20 are added as a stabilizer. Phosphate buffered saline ("PBS"), pH 7.4, is added to adjust the volume and standardize the activity units. The reaction mixture is fractionated by FPLC utilizing a Mono Q ® anion exchange column to isolate the fibrinolytic hybrid. Accordingly, 0.15 mg of the reaction mixture comprising the fibrin fragment and plasminogen activator is introduced into a Mono Q ® HR 5/5 column at a flow rate of 1 ml/min, gradient=2.5 mM/min NaCl. The mobile phase consists of 20 mM Tris-HCl, pH 7.4. The fibrinolytic hybrid is detected at 280 nm. The hybrid is subsequently purified on a benzamidine-agarose affinity matrix column. Thus the FPLC eluate is applied to a 1.5 ml benzamidine-agarose column (0.8×3.5 ml) and eluted with 0.05M sodium phosphate, 0.3M NaCl and 0.05% polysorbate 20, pH 7.4. t-PA molecules not bound by the benzamidine-agarose affinity matrix, non-functional fibrinolytic hybrids having impaired plasminogen activator portions, and free fibrin fragments are washed from the column with 8 column washes of equilibration buffer. The affinity matrix-bound fibrinolytic hybrids and uncomplexed t-PA are then eluted from the column with 0.1M acetate, 0.4M NaCl, pH 4.0. The purified complexes are assayed for functional activity by S-2251 chromogenic assay. Briefly, the complexes are incubated with plasminogen (0.04 U/ml) and the synthetic chromogenic substrate SS-2251 (3 mM) at 37° C. for 15 minutes. The reaction is stopped with 50% acetic acid. The absorbance of the reaction mixture is read at 405 nm. The activity of the complex may be derived from a curve created from the same assay using known amounts of t-PA.

While gel filtration HPLC may be substituted for FPLC, the latter is preferred because of the higher quality and purity of the product, better retentional of biological activity, greater ease of separation, greater speed, and minimal contamination by closely related fragments and molecules. The uniform size (dp=9.8 μm) and distribution of the anion exchanger material in the Mono Q ® column, and its small-ion capacity (0.28–0.36 mmol/ml), ensures its suitability for the herein-described purification process. In addition, low pressure chromatographic techniques are utilized in FPLC.

The following non-limiting example illustrates the preparation of a fragment DD/t-PA covalent hybrid according to the present invention, using a heterobifunctional cross linking reagent.

EXAMPLE 2

Fragment DD/t-PA Covalent Complex

One-chain t-PA (American Diagnostica, 0.5 mg containing 250,000 units of activity) is dissolved in 0.5 ml of PBS, pH 7.4. Immediately thereafter, SPDP in a 20-fold molar excess is added dropwise to the t-PA solution. This mixture is stirred gently at room temperature for 30 minutes and immediately dialyzed against a buffer (0.14M NaCl, 3.7 mM $NaH_2PO_4$, 1 mM KCl, pH 7.4) for 3 changes over 12 hours at 4° C. Fragment DD (10 mg/ml, 0.5 ml) is mixed in equal amounts (v/v) with a 1000-fold molar excess of 2-iminothiolane in 25 mm sodium borate, pH 9.3. The reaction is allowed to continue for 25 minutes at room temperature with gentle stirring. Excess 2-iminothiolane is immediately removed by gel filtration on Sephadex ® G-25 pre-equilibrated with PBS containing 0.02% sodium azide, pH 6.6. The SPDP-modified t-PA is then mixed with the 2-iminothiolated fragment DD, with gentle stirring at room temperature for 7 hours. At this time, a 100-fold molar excess of iodoacetamide to protein is added in 0.1M $NaH_2PO_4$, pH 8.0, in order to complete the reaction. Covalent complexes which contain intact fibrin binding sites of the parent fibrin fragment component, and intact catalytic sites of the parent plasminogen activator component, are purified from the reaction mixture in two steps. First, the mixture is subjected to benzamidine-agarose affinity chromatography as in Example 1. Second, immediately following elution from the benzamidine-agarose column and neutralization of the eluent, the fractions are applied to a fibrin-diatomaceous earth affinity column, which retains only conjugates containing fibrin fragments with fibrin-binding affinity, as well as uncoupled plasminogen activator. Species without fibrin affinity are not retained.

Cross-linked fibrin-diatomaceous earth (1.5 ml) is packed in a column (0.8×3.5 cm) and equilibrated with 0.05M sodium phosphate buffer, containing 0.3M NaCl and 0.05% polysorbate 80, pH 7.4. The eluted, neutralized fractions from the benzamidine-agarose chromatography are then applied to the fibrin-diatomaceous earth column. Fibrinolytic hybrids with impaired fibrin-binding function do not bind to the fibrin-diatomaceous earth affinity matrix. The matrix retains only hybrids containing intact fibrin fragments having fibrin-binding affinity, as well as uncoupled plasminogen activator. Species without fibrin affinity are not retained. The impaired, non-binding hybrids are washed from the column with 8 column volumes of the equilibration buffer. The bound proteins, that is, free plasminogen activator and hybrid molecules with intact fibrin binding function, are then eluted with equilibration buffer containing 0.5M arginine, 0.1 mg/ml human serum albumin, 0.01% polysorbate 80, and 25 KIU/ml aprotinin, pH 7.4. Arginine is removed from the eluate on a prepacked desalting column (Econo-Pac 10DG Column, Bio-Rad Corp., packed with Bio-Gel TM P-6 desalting gel, a hydrophilic polyacrylamide having a molecular weight exclusion limit of about 6 kDa and a hydrated particle size of about 90–180μ.) The eluate is then dialyzed against PBS with 0.02% sodium azide, pH 7.4. and stored in this buffer at 4° C. Where the plasminogen activator portion of the hybrid is t-PA or scu-PA uncoupled plasminogen activator may co-elute with the fibrinolytic hybrid upon fibrin-diatomaceous earth chromatography. Thus, co-eluted t-PA molecules are then separated from the hybrid molecules by an additional gel filtration step. The resulting fragment DD/t-PA covalent complex is then assayed for functional activity by S-2251 chromogenic assay, as in Example 1.

Plasminogen Activator-Fibrin Fragment Complex Activity

The ability of fibrin fragments to protect plasminogen activators against inactivation in plasma was demonstrated by the following series of experiments. According to a unique radiolabeled plasma clot lysis assay for plasminogen activator activity, activator sample (fibrinolytic hybrid or uncomplexed plasminogen activator) is collected and incubated with radiolabeled clot for 10 minutes. Solubilized radiolabeled fibrin is counted and expressed in terms of net percent of radioactivity released by the plasma clot into the supernatant. The amount of protein solubilized is calculated. The activator activity in units/ml of the sample is derived from a standard curve constructed utilizing t-PA or urokinase of known activity. The percent initial activity is calculated and plotted from the initial and residual activities.

Figure 2:
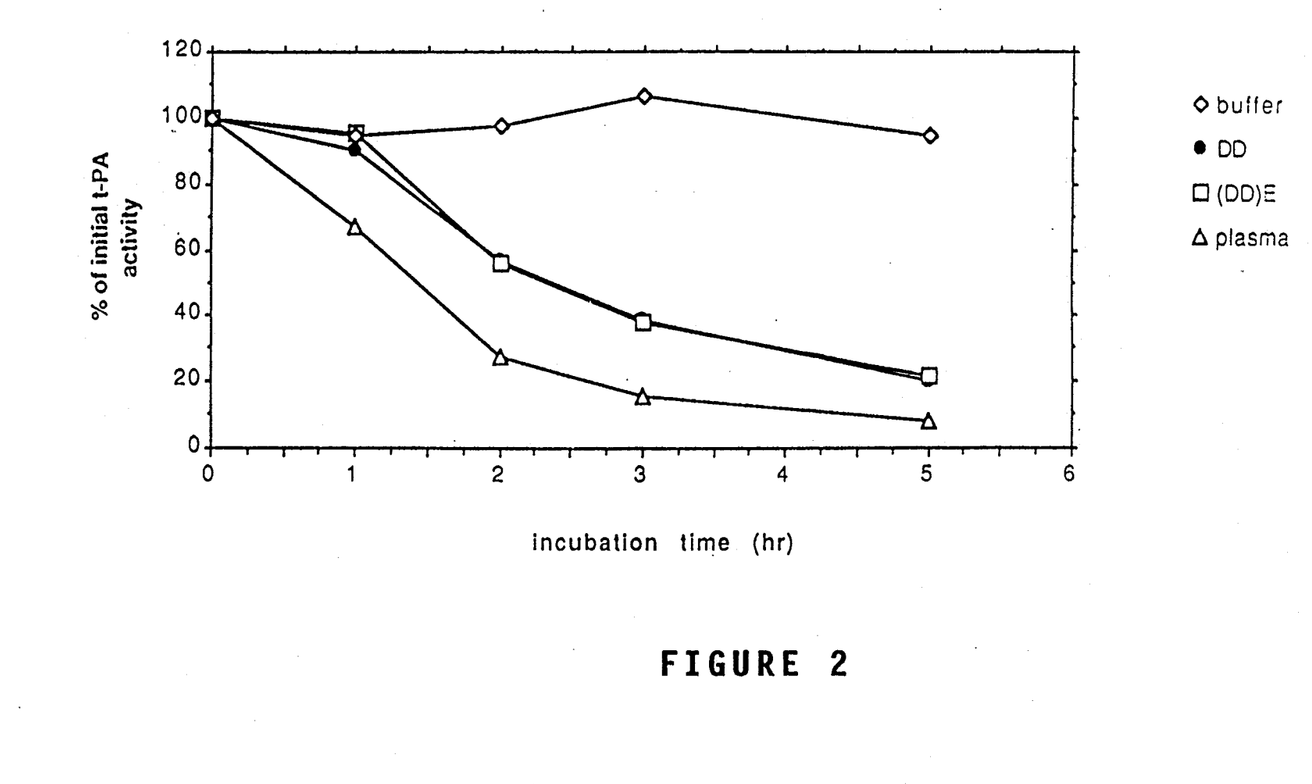
FIG. 2 is a plot of the duration of fibrinolytic activity of t-PA in plasma in the presence of fragment DD, (DD)E complex, or buffer (control). t-PA was complexed with a 500-fold molar excess of either fragment DD or (DD)E complex and incubated in normal human plasma for up to 5 hours. t-PA activity as a function of incubation time in plasma is expressed as a percentage of initial activity.

Fragment DD or the (DD)E complex was mixed with one-chain t-PA in a 500:1 molar ratio. The mixture was incubated in plasma for various periods of time. The remaining t-PA activity was measured. As shown in FIG. 2, t-PA in plasma lost its activity very rapidly, whereas t-PA stored in buffer retained its activity during 5 hours of incubation. Fragment DD and (DD)E complex conferred a protective effect on t-PA, such that the latter did not lose activity as rapidly as t-PA incubated in plasma alone. The half-life ("$T_{\frac{1}{2}}$") of t-PA in plasma (i.e., the time when t-PA activity is one-half its initial value), when protected with fragment DD or (DD)E complex, was 2.08 and 2.03 hours, respectively, as compared with 1.3 hours for unprotected t-PA. Thus, complexation with fibrin fragment resulted in about a 57% improvement in the half life of t-PA activity in plasma.

Figure 3:
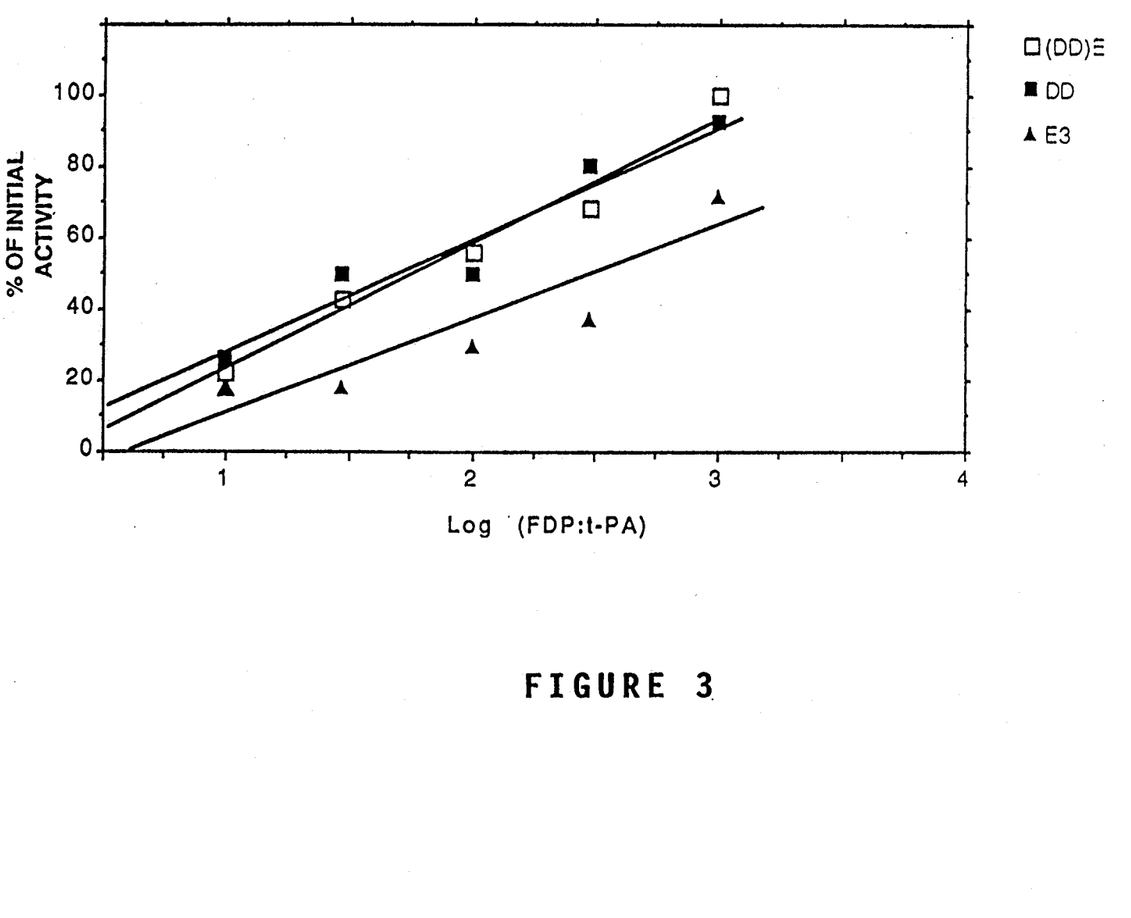
FIG. 3 is a plot of the fibrinolytic activity of t-PA as a function of the molar ratio of fibrin fragment to t-PA. The t-PA was incubated for 5 hours in normal human plasma either alone or complexed with various ratios of fragment DD, (DD)E complex or fragment $E_3$. The fibrinolytic activity remaining at t=5 hours as a function of the fibrin fragment:t-PA molar ratio (FDP:t-PA) is shown.

The protective effect afforded by the fibrin fragment may be influenced by the molar ratio between the fragment and the plasminogen activator, as demonstrated by the following experiment. t-PA was incubated in normal human plasma for 5 hours alone or in the presence of different molar excesses of the following fibrin fragments: (DD)E complex, fragment DD and fragment $E_3$. After the incubation time, residual t-PA activity was assayed. It was found that uncomplexed t-PA retained only 22% of its initial activity in plasma (data not shown) whereas near total original activity (92-100%) was preserved by complexation with fibrin fragments (FDP:t-PA=100:1 molar). See FIG. 3.

It has been reported that CNBr-cleavage fragments of human fibrinogen potentiate the rate of plasmin generation from plasminogen by t-PA, Neuwenhuizen et al. *Biochem. Biophys. Acta.* 755:531-533 (1983); Lijnen et al., *Eur. J. Biochem.* 144:541-544 (1984), and that the potentiating effect is attributable to fragment alpha 148-197 of the fibrinogen alpha chain. Neuwenhuizen et al. *Biochem. Biophys. Acta.* 748:86-92 (1983). Notwithstanding the presence of the same alpha chain segment in fragment D, in fragment DD, and in the (DD)E complex, CNBr-cleavage fragments of fibrinogen offer no protective effect on plasminogen activators in normal plasma, as determined by the following experiment.

Figure 4:
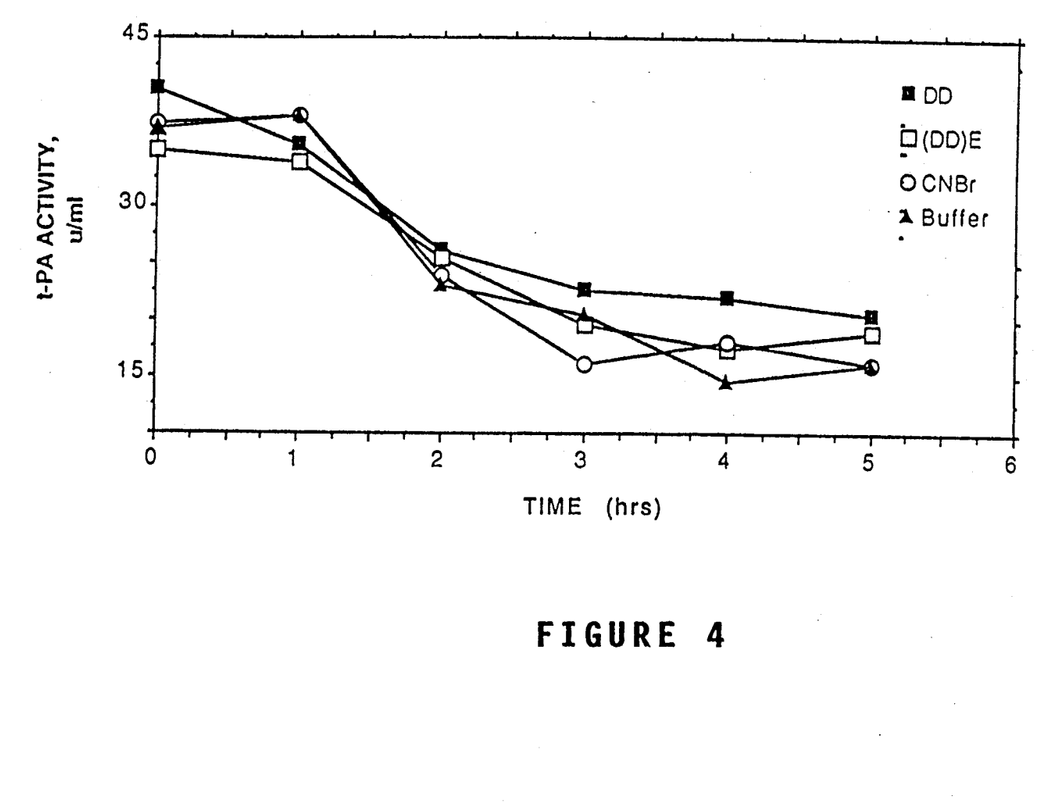
FIG. 4 is a plot of the duration of the fibrinolytic activity of t-PA in plasma in the presence of fragment DD, (DD)E complex, cyanogen bromide cleavage fragments of fibrinogen (CNBr), or buffer (control). The experimental conditions of complex formation and incubation are the same as those in FIG. 2.

One-chain t-PA was mixed with a 100-fold molar excess of (DD)E complex, fragment DD, or CNBr-cleavage fragments of fibrinogen and incubated at 37° C. for 45 minutes to allow complex formation. Normal human plasma was added and the mixture was incubated for various time intervals. The plasminogen activator activity as a function of time was measured by adding aliquots taken from the incubation mixtures at various times to human plasma supplemented with $^{125}$I-fibrinogen, immediately followed by the addition of thrombin and incubation at 37° C. for 10 minutes. The half-lives for fragment DD-protected t-PA, (DD)E complex-protected t-PA and unprotected t-PA were 4.87, 4.56 and 3.37 hours, respectively. While the two fibrin fragments exerted a slight protective effect on t-PA inactivation in plasma, the CNBr-cleavage fragments of fibrinogen were devoid of any protective effect. See FIG. 4.

Figure 5:
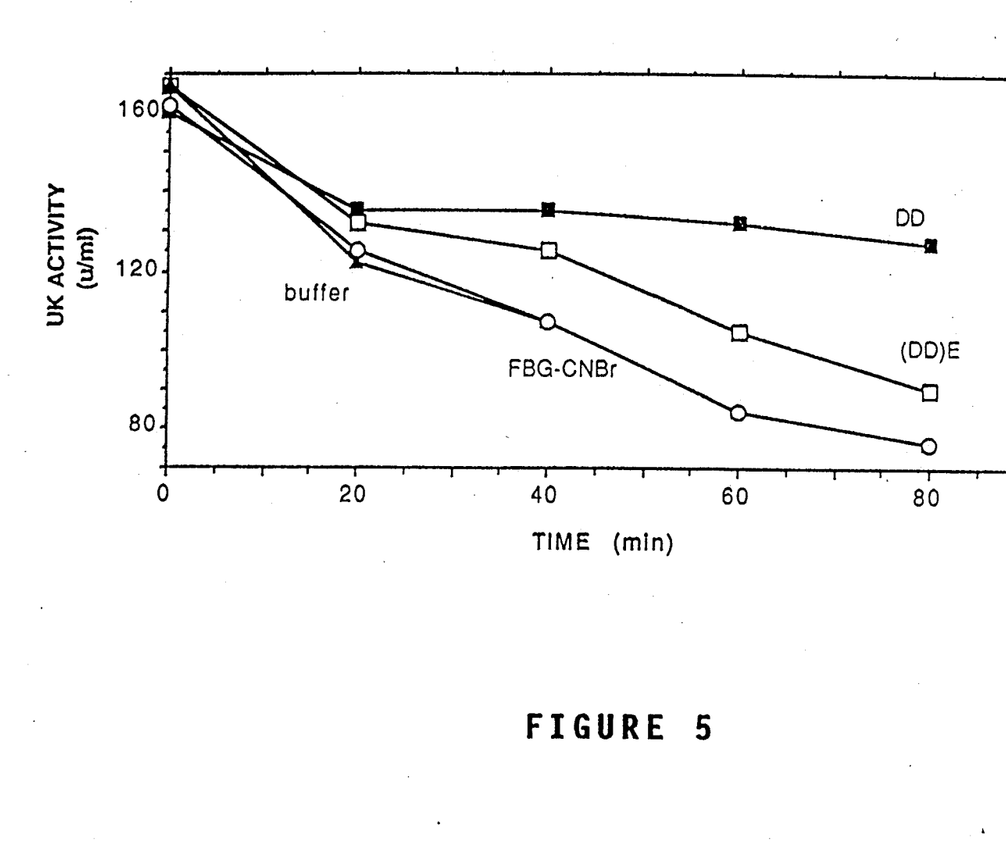
FIG. 5 is a plot of the duration of urokinase fibrinolytic activity in plasma in the presence of fragment DD, (DD)E complex, cyanogen bromide cleavage fragments of fibrinogen (CNBr), or buffer (control). The experimental conditions of complex formation and incubation are the same as those in FIG. 2.

Fibrin fragments have a similar protective effect on urokinase activity in plasma. Fragment DD, (DD)E complex or CNBr-cleavage fragments of fibrinogen were mixed in a 100-fold molar excess with urokinase and incubated at 37° C. for 45 minutes. The mixture was then added to 6 ml of plasma, and the incubation was continued. FIG. 5 shows that fragment DD and (DD)E complex provided a protective effect, while the CNBr-cleavage fibrinogen fragments provided no protective effect. The half-lives for DD- and (DD)E-protected urokinase were 4.6 and 1.6, respectively, while the half-life for unprotected urokinase was 1.2 hours. Complexation with fragment DD extends the half-life of urokinase almost four-fold.

Figure 6:
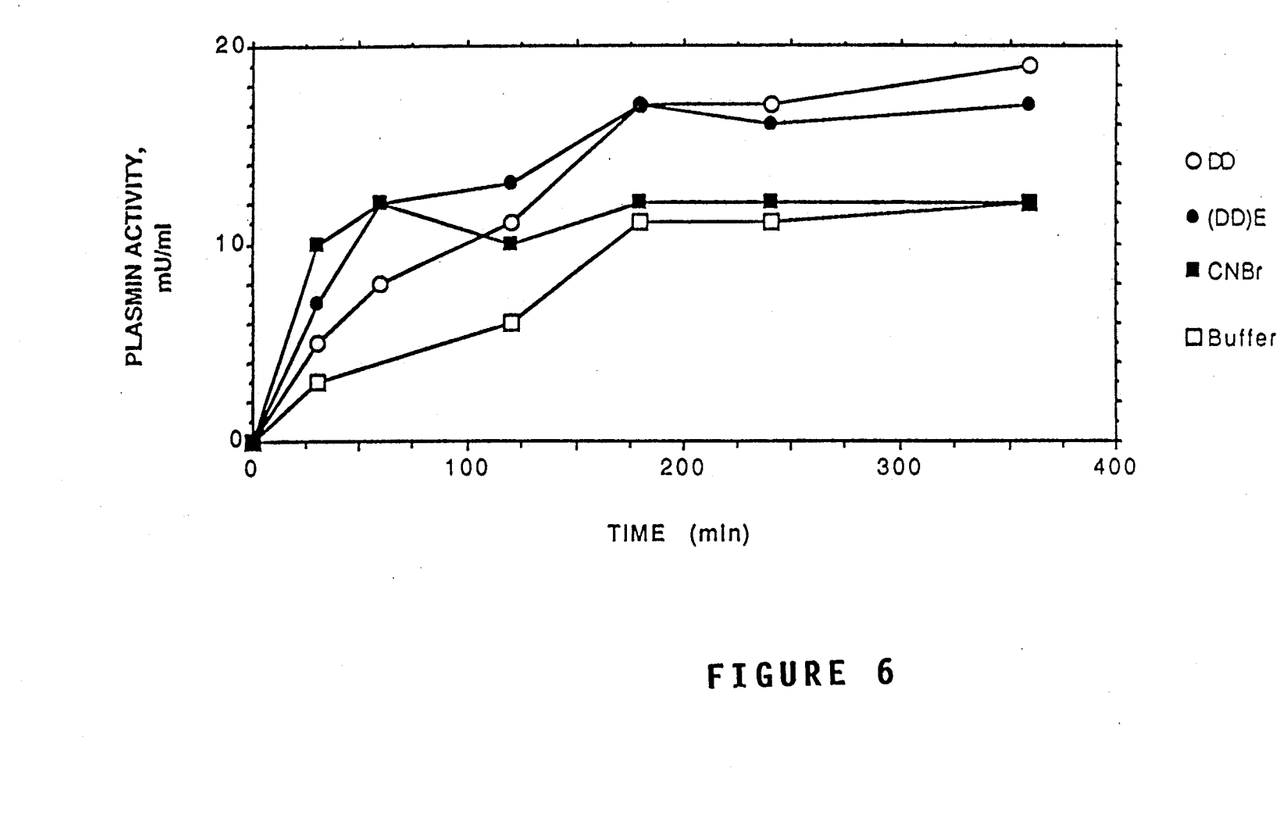
FIG. 6 is a plot of plasmin generation by t-PA in the presence of fragment DD, (DD)E complex, cyanogen bromide cleavage fragments of fibrinogen (CNBr), or buffer (control). Plasmin activity was determined at various intervals from hydrolysis of the chromogenic substrate S-2251.

The fibrinolytic hybrids of the invention accelerate plasmin generation at a rate almost two-fold higher than CNBr-cleavage fragments of fibrinogen. The latter are known accelerators of plasminogen activation. One-chain t-PA was incubated with a 100-fold molar excess of fragment DD, (DD)E complex or CNBr-cleavage fragments of fibrinogen to form non-covalent complexes. Plasminogen and the chromogenic substrate S2251 were added to each mixture and incubated at 37° C. for different time intervals, according to the method of Friberger et al., *Haemostasis* 7:138-145 (1978). The amount of plasmin generated was recorded from absorbance at 405 nm, and the activity in milliunits per ml was determined from a standard curve. The results are shown in FIG. 6. While CNBr-cleavage fragments of fibrinogen were more potent than fibrin fragments in accelerating the rate of plasmin generation over brief incubation times (up to 60 minutes), the reverse was observed at longer incubation times.

In clinical applications, the thrombolytic hybrids of the present invention will generate more plasmin on fibrin surfaces from a given amount of plasminogen than the activator molecule may generate in the absence of the fibrin fragment. This permits the use of a lower amount of activator than presently used in clinical practice.

Figure 7:
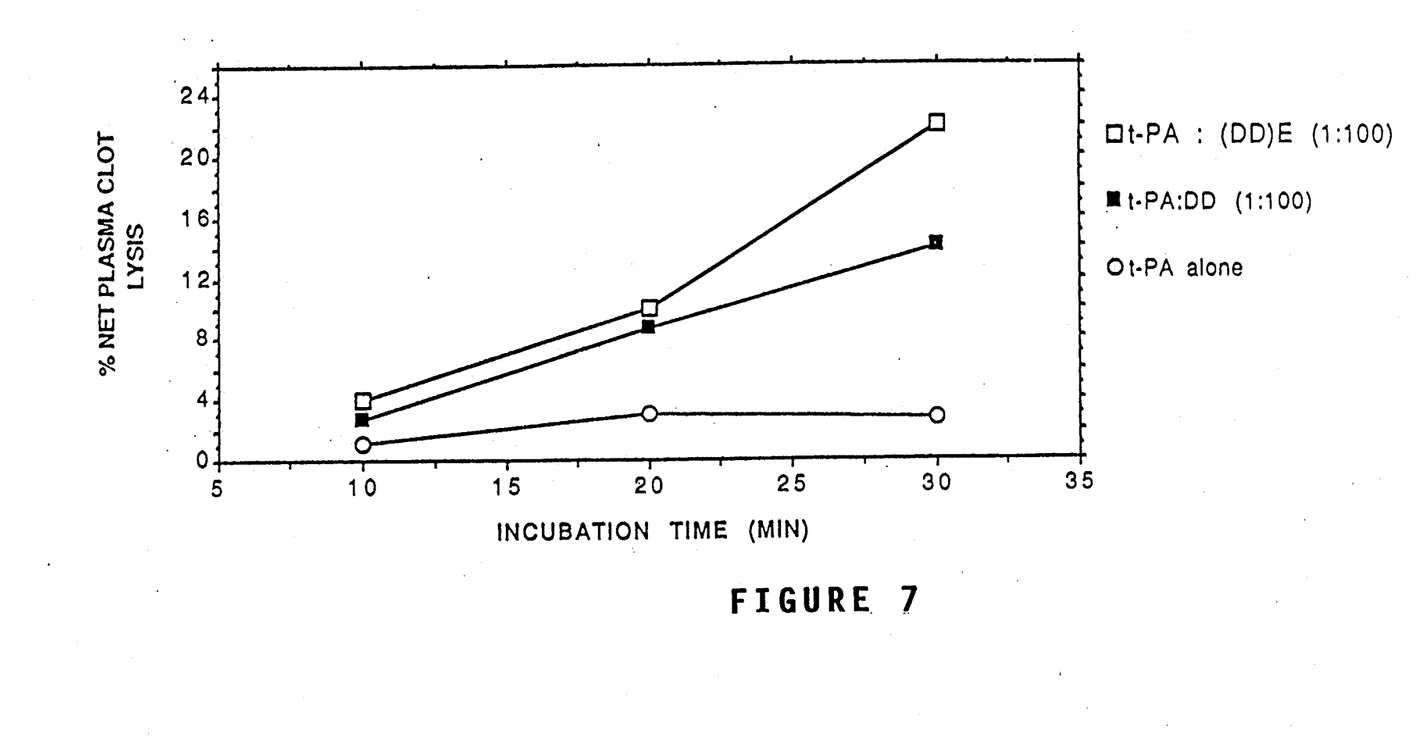
FIG. 7 is a plot of fibrin clot lysis by either t-PA alone, or t-PA complexed with fragment DD or (DD)E complex in a 1:100 molar ratio. The lytic agents were incubated in human plasma at 37° C. for 1 hour. The mixture was then supplemented with $^{125}$I-fibrinogen and clotted with thrombin. Clot lysis, measured at various time intervals, is plotted as a percentage of initial values. The top curve (solid circles) was obtained using t-PA with no plasma preincubation.

The hybrids accelerate lysis of plasma clots, as observed from the following experiment. Ten units of one-chain t-PA were added to 1 ml of normal human citrated plasma containing $^{125}$I-fibrinogen and incubated at 37° C. for 1 hour. Lysis of the plasma clot was measured by release of radioactivity counts into the supernatant. As shown in FIG. 7, only 2.9% of the clot was lysed. When the same amount of plasma was clotted without pre-incubation with t-PA, the same amount of t-PA achieved dissolution of 24.3% of the clot. Thus, there was a significant inactivation of t-PA by the plasma milieu.

Fibrinolytic complexes of one-chain t-PA were then formed with a 10-fold excess of either DD or (DD)E, and were added to plasma. Following incubation at 37° C. for 1 hour, the plasma was clotted by addition of thrombin. As shown in FIG. 7, the fibrinolytic complexes of the invention caused a significantly greater plasma clot lysis than plasminogen activator alone. While the lytic activity of naked plasminogen activator molecules is rapidly suppressed in plasma, complexation with fibrin fragments has a substantial protective effect from inhibitors found in plasma.

The thrombolytic hybrids of the invention, due to their fibrin specificity, readily localize at the fibrin surface of thrombi. As a result, only clot-surface bound plasminogen is activated, without significant systemic plasminogen activation and possible inducement of a lytic state. The risk of hemorrhagic complication is thus reduced. Moreover, the thrombus-targeting property of the hybrids will provide a thrombolytic effect of comparable degree to locally infused thrombolytic agent.

The hybrids are strong potentiators of plasminogen activation, providing more plasmin from the same amount of plasminogen than naked plasminogen activator. Moreover, the fibrin component of the hybrid affords considerable protection against inhibition of the plasminogen activator component by inhibitors present in the blood, and protection against rapid uptake by the liver, contributing to an increased half-life of activity compared to uncomplexed plasminogen activator. Substitution of the thrombolytic hybrids of the invention for the presently available plasminogen activators will permit clinicians to decrease the frequency, duration and dosage of administration of therapeutic agent without sacrificing efficacy. Treatment with the hybrids will permit the clinician to lower the dose and delay the initiation of heparin therapy and other anticoagulant therapies for the prevention of restenosis and fresh clot formation (reocclusion).

The thrombolytic hybrids of the invention may be administered intravascularly or intramuscularly in the form of a composition containing the hybrid and a pharmaceutically acceptable carrier suitable for intravascular or intramuscular administration. The composition may be in the form of a solution in a suitable carrier, for example isotonic saline and sterile water. The composition may further include any of the additives typically utilized in intravascular or intramuscular administration, e.g. buffer salts, L-arginine, glucose, etc. The composition may contain stabilizers such as, for example, human serum albumin or non-ionic detergents such as polysorbate.

The dosage, expressed in terms of units of plasminogen activator, is generally less than the dosages presently used for corresponding uncomplexed plasminogen activator. It is contemplated that the hybrids of the invention may be utilized in dosages as much as an order of magnitude lower than the corresponding uncomplexed plasminogen activator.

Presently, the typical dosage practices for administering the principal plasminogen activators are as follows:

| t-PA or scu-PA: | One hundred mg (60 mg bolus, 20 mg infusion in first hour, then 20 mg infusion in next hour); |
|---|---|
| streptokinase or urokinase: | 1.5 million units (bolus, infusion over three hours) |

It is contemplated that the same affect may be obtained by administering only one tenth the standard dosage, when the plasminogen activator is coupled to a fibrin fragment according to the present invention. Thus, it is contemplated that 10 mg of t-PA or scu-PA, or 150,000 units of streptokinase or urokinase, is an effective dosage when administered in the form of a fibrinolytic hybrid.

The hybrids of the invention may be utilized in any situation where the corresponding uncomplexed plasminogen activator is utilized, e.g., in the treatment of myocardial infarctions, pulmonary emboli, deep venous thrombosis, etc. where vascular thrombi are to be dissolved.

The invention has been illustrated by the covalent or non-covalent linkage of fibrin fragments with appropriate plasminogen activators to form fibrinolytic hybrids. Also within the scope of the invention is preparation of a single unitary polypeptide having the properties of the fibrinolytic hybrids described herein, which polypeptides are prepared by genetic engineering techniques. Thus, it is contemplated that genetic information coding for a fibrin fragment and information coding for a plasminogen activator may, by DNA recombinant techniques, be co-expressed as a single unitary molecule having the properties of the fibrinolytic hybrids described herein.

The present invention may be embodied in other specific forms without departing from the spirit or essential attributes thereof and, accordingly, reference should be made to the appended claims, rather than to the foregoing specifications, as indicating the scope of the invention.

We claim:

1. A thrombolytic agent comprising a non-covalent complex formed from contacting tPA with a 100–500 molar excess of either fibrin fragment DD or fibrin fragment DD(E).

2. A thrombolytic agent according to claim 1, wherein tPA is complexed with fibrin fragment DD.

3. A thrombolytic agent according to claim 1, wherein tPA is complexed with fibrin fragment DD(E).

4. A thrombolytic agent comprising tPA covalently linked to either fibrin fragment DD or fibrin fragment DD(E).

5. A thrombolytic agent according to claim 4, wherein tPA is covalently linked to fibrin fragment DD.

6. A thrombolytic agent according to claim 4, wherein tPA is covalently linked to fibrin fragment DD(E).

7. A thrombolytic agent according to claim 4, wherein tPA and either fibrin fragment DD or fibrin fragment DD(E) are covalently linked by a homobifunctional cross-linking agent.

8. A thrombolytic agent according to claim 4, wherein tPA and either fibrin fragment DD or fibrin fragment DD(E) are covalently linked by a heterobifunctional cross-linking agent.

9. A thrombolytic agent according to claim 8, wherein said heterobifunctional cross-linking agent is selected from the group consisting of N-succinimidyl-3-(2-pyridyldithio)propionate and sulfosuccinimidyl-2-(p-azidosalicylamido)ethyl-1-3'-dithiopropionate.

10. A composition comprising a pharmaceutically effective amount of a thrombolytic agent according to claim 1 and an inert pharmaceutically acceptable carrier or diluent.

11. A composition according to claim 10, wherein said carrier or diluent is suitable for intravascular or intramuscular administration.

12. A composition comprising a pharmaceutically effective amount of a thrombolytic agent according to claim 4 and an inert pharmaceutically acceptable carrier or diluent.

13. A composition according to claim 12, wherein said carrier or diluent is suitable for intravascular or intramuscular administration.

14. A method for dissolving vascular thrombi comprising administering a composition according to claim 10 to a mammal.

15. A method for dissolving vascular thrombi comprising administering a composition according to claim 12 to a mammal.

* * * * *